United States Patent [19]

Sathe

[11] Patent Number: 4,565,890

[45] Date of Patent: Jan. 21, 1986

[54] PROCESS FOR THE PREPARATION OF N-ACETYL-P-AMINOPHENOL

[75] Inventor: Sharad S. Sathe, Manchester, Mo.

[73] Assignee: Mallinckrodt, Inc., St. Louis, Mo.

[21] Appl. No.: 546,051

[22] Filed: Oct. 27, 1983

[51] Int. Cl.$^4$ .......................................... C07C 103/127
[52] U.S. Cl. .................................. 564/216; 564/223; 564/439
[58] Field of Search .................... 564/216, 223, 439

[56] References Cited

U.S. PATENT DOCUMENTS

| | | | |
|---|---|---|---|
| 2,799,692 | 7/1957 | Croxall et al. | 564/223 X |
| 3,042,719 | 7/1962 | Hahn et al. | 564/216 |
| 3,113,150 | 12/1963 | Young | 564/216 X |
| 3,130,223 | 4/1964 | Surine et al. | 564/223 X |
| 3,658,905 | 4/1972 | Daunis et al. | 564/439 X |
| 3,694,508 | 9/1972 | Baron et al. | 564/223 X |
| 3,845,129 | 10/1974 | Reid | 564/439 |
| 3,876,703 | 4/1975 | Harmetz et al. | 564/439 X |
| 4,440,954 | 4/1984 | Clingan et al. | 564/439 |

*Primary Examiner*—Robert V. Hines
*Attorney, Agent, or Firm*—Senniger, Powers, Leavitt and Roedel

[57] ABSTRACT

An improved process for the preparation of N-acetyl-p-aminophenol. p-Aminophenol is acetylated in an aqueous medium to produce a crude aqueous reaction mixture and N-acetyl-p-aminophenol product is recovered by crystallization from an aqueous system comprising the reaction mixture. Crystals are separated from the crude mother liquor which contains residual N-acetyl-p-aminophenol and unreacted acetic acid. According to the improvement, residual N-acetyl-p-aminophenol and acetic acid are recovered from the crude mother liquor by liquid-liquid extraction with a water-immiscible organic solvent to produce an extract containing N-acetyl-p-aminophenol and acetic acid. The extract is distilled to strip off the solvent and acetic acid.

27 Claims, 1 Drawing Figure

PROCESS FOR THE PREPARATION OF N-ACETYL-P-AMINOPHENOL

BACKGROUND OF THE INVENTION

This invention relates to the preparation of N-acetyl-p-aminophenol by acetylation of p-aminophenol in an aqueous medium, and more particularly, to an improved process for the recovery of N-acetyl-p-aminophenol from the aqueous medium.

The analgesic N-acetyl-p-aminophenol, commonly known in the art as acetaminophen or "APAP", is commercially prepared by reaction of p-aminophenol ("PAP") with acetic anhydride in an acidic aqueous medium. p-Aminophenol is conventionally prepared by catalytic hydrogenation of nitrobenzene in a mineral acid system. After purification of the reaction product for removal of residual impurities such as 4,4'-diaminodiphenyl ether, the p-aminophenol is precipitated as its alkali metal salt by addition of a caustic solution or an alkali metal carbonate or bicarbonate. The precipitated product is redissolved in acetic acid solution and acetic anhydride added for acetylation of the PAP to APAP.

In the co-pending and co-assigned application of William R. Clingan et al, Ser. No. 251,461, filed Apr. 20, 1981, a process is described for extractive removal of 4,4'-diaminodiphenyl ether and related impurities from the aqueous reaction product obtained upon catalytic hydrogenation of nitrobenzene to PAP. Use of this process reduces the level of impurities to be dealt with in the acetylation of PAP to APAP. Irrespective of what process is used for preparation and refining of the intermediate PAP, APAP is produced by acetylation of PAP in an acidic aqueous solution.

APAP is recovered from the reaction solution by crystallization and filtration or centrifugation, yielding a mother liquor that remains saturated in APAP and contains a substantial proportion of acetic acid. Unless this crude mother liquor is subjected to further processing for recovery of at least a portion of the APAP and acetic acid remaining in the solution, a substantial yield loss may be suffered. Commercially acetic acid has been recovered by distillation of the crude mother liquor, leaving a residue which may be crystallized for recovery of a second crop of APAP crystals. However, in this commercial practice, the acetic acid fraction recovered typically has a strength of only about 20% by weight to 25% by weight which limits the uses to which it can be put, and its value. Color bodies in the mother liquor are concentrated in the distillation residue and tend to impart an undesirably strong color to the second crop of APAP crystals. Additionally, corrosion problems may be encountered in distillation of the mother liquor due to the presence of sulfur dioxide released from the bisulfate salts conventionally added to an APAP crystallization system to protect the APAP product against air oxidation.

SUMMARY OF THE INVENTION

Among the several objects of the present invention therefore, may be noted the provision of an improved process for the preparation of APAP; the provision of such a process in which APAP is produced in high yield; the provision of an improved process in which acetic acid of high strength and purity may be recovered from the crude mother liquor; the provision of such a process which minimizes corrosion problems in recovery of acetic acid; and the provision of such a process in which a high quality APAP product is produced.

Briefly, therefore, the present invention is directed to an improvement in a process for the preparation of APAP by acetylation of PAP in an aqueous medium to produce a crude aqueous reaction mixture, recovering APAP product by crystallization from an aqueous system comprising the reaction mixture, and separating the crystals from the crude mother liquor, the mother liquor containing residual APAP and acetic acid. The improvement comprises recovering residual APAP and acetic acid from the crude mother liquor by liquid-liquid extraction with a water-immiscible organic solvent, thereby producing an extract containing APAP and acetic acid. The extract is distilled to strip off the solvent and acetic acid.

The invention is further directed to such a process in which the residue from the distillation is mixed with water to reduce solubility of APAP in the residue, and the resultant mixture is cooled to crystallize APAP therefrom and produce a secondary mother liquor. Crystallized APAP is separated from the secondary mother liquor.

Other objects and features will be in part apparent and in part pointed out hereinafter.

BRIEF DESCRIPTION OF THE DRAWING

The single FIGURE of the drawing is a schematic flow sheet for the improved process of the invention.

DESCRIPTION OF THE PREFERRED EMBODIMENTS

Figure 1:
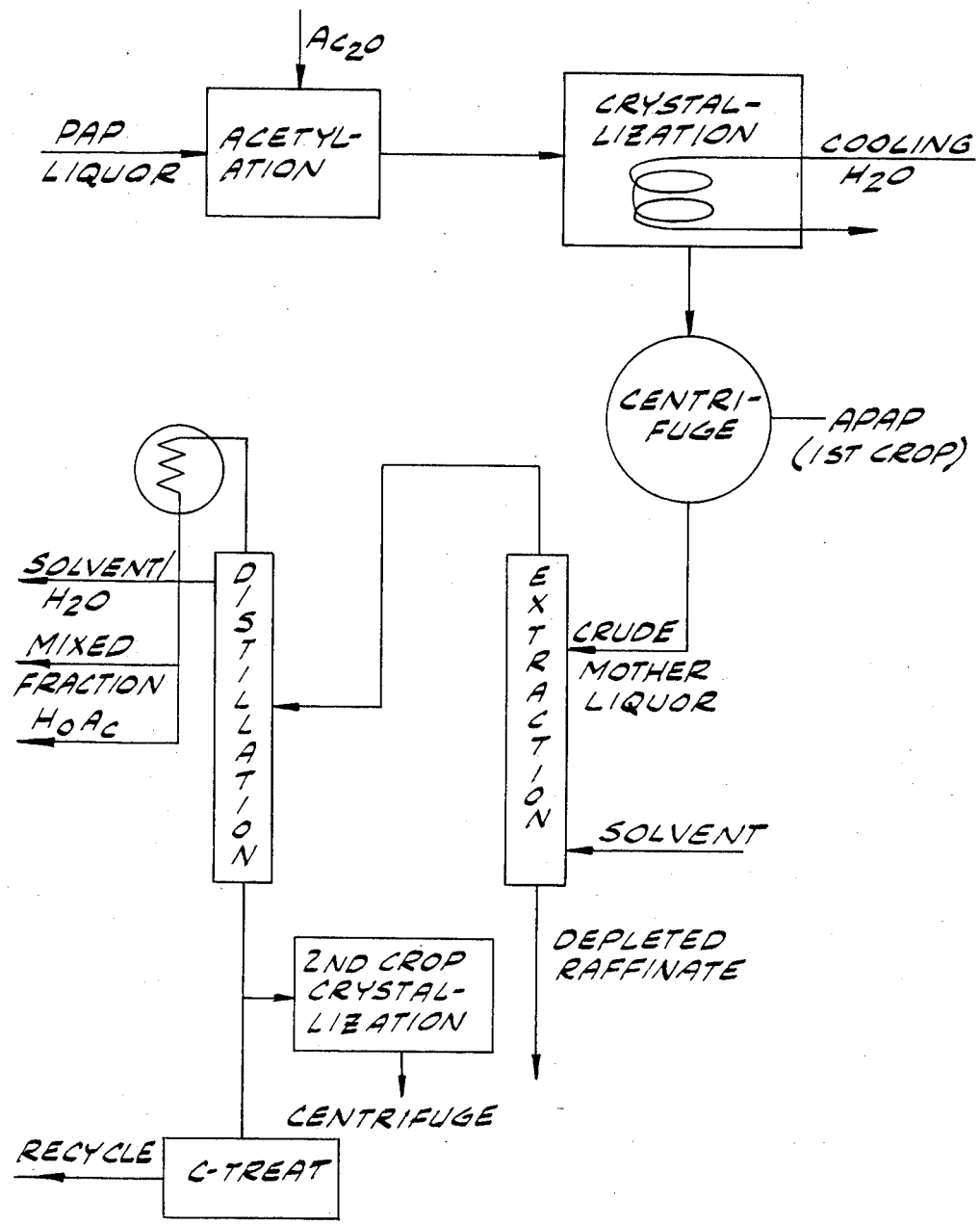

In accordance with the present invention, an improved process has been discovered for recovering acetic acid from the crude mother liquor obtained upon the crystallization of APAP from the reaction mixture that is produced in the acetylation of PAP. In the improved process, both acetic acid and residual APAP are removed from the crude mother liquor by liquid-liquid extraction and the acetic acid thereafter recovered from the extract by distillation, leaving a residue containing APAP that may be either recycled or subjected to further crystallization for recovery of a second crop of APAP crystals.

Illustrated in the single FIGURE of the drawing is a schematic flow sheet of the improved process of the invention. In this process, the slurry obtained by crystallization of APAP from the acetylation reaction mixture is centrifuged to produce the primary APAP product and a filtrate which is subjected to liquid-liquid extraction. Any of a variety of conventional water-immiscible organic solvents can be used for the extraction. However, to allow recovery of substantially pure acetic acid the solvent should have a volatility which differs significantly from the volatility of acetic acid. It is further preferred that the solvent not form an azeotrope with acetic acid. Preferably the solvent should have a boiling point which differs by at least about 20° C. from 118° C., the boiling point of acetic acid. Those solvents having a greater volatility than acetic acid are more preferred. Solvents which may be used include halogenated solvents such as methylene dichloride, ethylene dichloride, and chloroform, ketones such as methyl ethyl ketone, methyl isopropyl ketone, and methyl isoamyl ketone, and substantially water-immiscible alcohols such as hexanol and amyl alcohol. Preferably, however, the solvent is an ester of a lower alcohol and a low-molecular weight alkanoic acid such as ethyl acetate, ethyl proprionate, methyl proprionate, methyl acetate, and butyl proprionate, propyl formate, and propyl acetate. Ethyl acetate is particularly preferred.

Extraction may be carried out by contacting the crude mother liquor with the solvent in conventional equipment such as, for example, a stirred mixer/settler. Preferably, extraction is conducted in a continuous countercurrent extraction system having a plurality of equilibrium stages and comprising means for promoting mass transfer between the solvent phase and the aqueous phase. Thus, the extraction may be carried out in a vertical-packed column or in a centrifugal extractor such as that sold under the trade designation "Podbielniak" by Baker-Perkins, or "DeLaval" by TransAmerican DeLaval, Inc. Preferably, however, the extraction is carried out in a reciprocating plate column containing between about five and about ten equilibrium stages.

While the temperature of extraction is not critical, it should be below the temperature at which significant mutual solubility of water and solvent is incurred. This temperature varies with the identity of the solvent. Generally, however, satisfactory results are achieved where the extraction is carried out at a temperature in a range of about between 0° C. and about 30° C.

By countercurrent extraction using a plurality of stages, over 90% of the APAP contained in the mother liquor can be transferred to the extract. Recovery of acetic acid is even more efficient and can exceed 99%. Thus, aqueous raffinate from the extraction, which contains ammonium salts, sulfur dioxide, and color bodies can be discarded.

The extract is subjected to distillation for recovery of the solvent and acetic acid, leaving a residue containing APAP which can be recycled or subjected to crystallization for recovery of a second crop of APAP.

In the distillation step, at least two separate overhead fractions are preferably recovered, one comprising principally solvent and water, and the other comprising principally acetic acid and water. Where, for example, a relatively volatile solvent such as ethyl acetate is used for the extraction, the most volatile fraction recovered in the distillation comprises solvent and water, while a distinctly higher boiling fraction is substantially free of solvent and comprises a high concentration of acetic acid in water. In order to obtain a clean separation an intermediate fraction, which comprises a mixture of all of three of the vaporized components, may be collected. The volatile fraction comprising solvent and water may be allowed to separate into a solvent layer and an aqueous layer, and the solvent decanted for recycle to the extraction step. The fraction comprising a high concentration of acetic acid in water is removed from the process and used as a source of acetic acid in other operations. Where an intermediate fraction is obtained comprising solvent, water, and acetic acid, the solvent may also be decanted and recycled and the aqueous phase, comprising a relatively dilute solution of acetic acid and water, may be used in other processing operations or discarded.

Distillation is conveniently carried out batchwise to facilitate recovery of fractions of the desired composition. However, in a high volume operation a continuous distillation column may be used with recovery of sidestreams of the desired fractions. Whether batch or continuous, distillation may be conveniently carried out at atmospheric pressure, for example, in a packed column containing at least one transfer unit. Distillation conditions are readily controlled to provide an aqueous acetic acid fraction having an acid strength of 65% by weight or greater. If a column comprising five or more transfer units is utilized, glacial acetic acid may be recovered.

The bottom fraction obtained in the distillation contains APAP and typically about 25% by weight acetic acid and may be subjected to crystallization for recovery of a second crop of APAP or, alternatively, recycled to the primary crystallization step. Where a second crop of crystals is desired, the bottom fraction is mixed with water to depress APAP solubility and then cooled to ambient temperature or somewhat below in order to crystallize APAP. Although the amount of water mixed with the bottom fraction is not highly critical, it is preferably between about 0.7 parts by volume and about 1.3 parts by volume per part by volume of the bottom fraction. Roughly equal volumetric proportions are most preferred. If desired, the mixture of water and bottom fraction may be refrigerated for crystallization, but the marginal increase in yield thereby obtained may not justify refrigeration in many cases.

After crystallization is complete, the resultant slurry of APAP in secondary mother liquor is fed to a centrifuge or a filter for recovery of the second crop of crystals. The crystals are preferably washed with cold water and dried under vacuum. In an alternative embodiment of the invention, as noted above, the bottom fraction obtained by the distillation step may be recycled to the primary crystallization step for recovery of further amounts of APAP. Where the bottom fraction is recycled, it is preferably treated by adsorption for removal of residual amounts of impurities. Adsorption of impurities from the bottom fraction is carried out by contacting the fraction with an adsorbent such as activated carbon. Alternatively, other adsorbents known to the art, such as clay, may be used for treatment of the bottom fraction prior to recycle. As a further alternative, the bottom fraction may be passed through an ion exchange column for separation of impurities.

The following example illustrates the invention.

EXAMPLE

APAP was prepared by acetylation of PAP in aqueous acidic solution. This solution was cooled for crystallization of APAP and the crude mother liquor separated by centrifugation.

An aliquot of the APAP mother liquor (500 mL) was contacted under agitation with ethyl acetate (200 mL) and the phases allowed to separate. The extract phase was removed and the aqueous phase extracted with two additional portions of ethyl acetate (200 mL each). The three extracts were combined and subjected to fractional distillation at atmospheric pressure. The following fractions were collected:

| Temperature (°C.) | Volume (mL) | Composition |
|---|---|---|
| 70–81 | 590 | Ethyl Acetate + Water |
| 81–94 | 37 | Ethyl Acetate + Water + Acetic Acid |
| 94–106 | 62 | Acetic Acid + Water |

Approximately 30 mL to 40 mL of distillation heel remained in the distillation pot. This heel was allowed to cool slightly, after which deionized water (35 mL) was added slowly to the pot. APAP started to crystallize as water was added. The slurry was cooled to 20° C. and the crystalline APAP obtained was collected on a filter. These crystals were washed with cold water and thereafter dried at 70° C. under vacuum. Yield of APAP was 9.1 g, 57% based on the APAP content of the crude mother liquor.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. In a process for the preparation of N-acetyl-p-aminophenol which comprises acetylation of p-aminophenol in an aqueous medium to produce a crude aqueous reaction mixture, recovery of the N-acetyl-p-aminophenol product by crystallization from an aqueous system comprising the reaction mixture, and separation of the crystals from the crude mother liquor, said mother liquor containing residual N-acetyl-p-aminophenol and unreacted acetic acid, the improvement comprising recovering residual N-acetyl-p-aminophenol and acetic acid from the crude mother liquor by liquid-liquid extraction with a water immiscible organic solvent, thereby producing an extract containing N-acetyl-p-aminophenol and acetic acid; and distilling said extract to strip off said solvent and acetic acid.

2. The process as set forth in claim 1, the improvement comprising the further steps of:
mixing the residue from said distillation with water to reduce the solubility of N-acetyl-p-aminophenol in the residue;
cooling the resultant mixture of distillation residue and water to crystallize N-acetyl-p-aminophenol therefrom and produce a secondary mother liquor; and
separating the crystallized N-acetyl-p-aminophenol from the secondary mother liquor.

3. The process of set forth in claim 2 wherein said solvent is selected from the group consisting of esters, ketones, alcohols and halogenated solvents.

4. The process as set forth in claim 3 wherein said solvent comprises a lower alkyl ester of a low molecular weight alkanoic acid.

5. The process as set forth in claim 4 wherein the extraction is carried out at a temperature of between about 0° C. and about 30° C.

6. The process as set forth in claim 2 wherein N-acetyl-p-aminophenol and acetic acid are recovered from said crude mother liquor by continuous countercurrent extraction.

7. The process as set forth in claim 6 wherein said extraction is conducted in a fractional liquid-liquid extraction system comprising at least five equilibrium stages.

8. The process as set forth in claim 7 wherein said system comprises a reciprocating plate column.

9. The process as set forth in claim 2 wherein an overhead fraction comprising said solvent is recovered in the distillation of said extract.

10. The process as set forth in claim 9 wherein said solvent is separated from any aqueous phase in said fraction, and the solvent is recycled for use in said extraction.

11. The process as set forth in claim 2 in which said solvent comprises an ester having a boiling point not higher than 98° C., and an overhead fraction comprising a concentrated solution of acetic acid substantially free of said solvent is recovered in said distillation.

12. The process as set forth in claim 11 wherein a substantially solvent-free overhead fraction comprising at least about 65% by weight acetic acid is recovered in said distillation.

13. The process as set forth in claim 12 wherein said acetic acid fraction comprises glacial acetic acid.

14. The process as set forth in claim 1 wherein the improvement further comprises contacting the residue from said distillation with an adsorbent for removal of impurities therefrom.

15. The process as set forth in claim 14 wherein the improvement further comprises combining the purified residue with a further portion of said crude reaction mixture for recovery of N-acetyl-p-aminophenol by crystallization.

16. The process as set forth in claim 14 wherein said solvent is selected from the group consisting of esters, ketones, alcohols and halogenated solvents.

17. The process as set forth in claim 16 wherein said solvent comprises a lower alkyl ester of a low molecular weight alkanoic acid.

18. The process as set forth in claim 17 wherein the extraction is carried out at a temperature of between about 0° C. and about 30° C.

19. The process as set forth in claim 14 wherein N-acetyl-p-aminophenol and acetic acid are recovered from said crude mother liquor by continuous countercurrent extraction.

20. The process as set forth in claim 19 wherein said extraction is contacted in a fractional liquid-liquid extraction system comprising at least five equilibrium stages.

21. The process as set forth in claim 20 wherein said system comprises a reciprocating plate column.

22. The process as set forth in claim 14 wherein an overhead fraction comprising said solvent is recovered in the distillation of said extract.

23. The process as set forth in claim 22 wherein said solvent is separated from any aqueous phase in said fraction, and the solvent is recycled for use in said extraction.

24. The process as set forth in claim 14 wherein said solvent comprises an ester having a boiling point not higher than about 98° C., and an overhead fraction comprising a concentrated solution of acetic acid substantially free of said solvent is recovered in said distillation.

25. The process as set forth in claim 24 wherein a substantially solvent-free overhead fraction comprising at least about 65% by weight acetic acid is recovered in said distillation.

26. The process as set forth in claim 25 wherein said acetic acid fraction comprises glacial acetic acid.

27. In a process for the preparation of N-acetyl-p-aminophenol which comprises acetylation of p-aminophenol in an aqueous medium to produce a crude aqueous reaction mixture, recovery of the N-acetyl-p-aminophenol product by crystallization from an aqueous system comprising the reaction mixture, and separation of the crystals from the crude mother liquor, said mother liquor containing residual N-acetyl-p-aminophenol and unreacted acetic acid, the improvement comprising recovering residual N-acetyl-p-aminophenol and acetic acid from the crude mother liquid by liquid/liquid extraction with a water immiscible organic solvent, thereby producing an extract containing N-acetyl-p-aminophenol and acetic acid.

* * * * *